Feb. 20, 1973 B. L. COBIA Plant Pat. 3,307

MILKWEED PLANT

Filed May 18, 1971

INVENTOR
BARNELL L. COBIA
BY Roger L. Martin
ATTORNEY

United States Patent Office

Plant Pat. 3,307
Patented Feb. 20, 1973

3,307
MILKWEED PLANT

Barnell L. Cobia, 135 Temple Grove Drive,
Winter Garden, Fla. 32787

Filed May 18, 1971, Ser. No. 144,691
Int. Cl. A01h 5/00
U.S. Cl. Plt.—88 1 Claim

ABSTRACT OF THE DISCLOSURE

A new and distinct plant variety of the milkweed family has a loose growth habit providing specimens with stems and petioles with certain color characteristics, a wavy splotched and/or streaked variegated leaf blade with certain color characteristics involving relatively long lasting red-purple, red and/or yellow-red hues, and an inflorescence with mixtures of 5-merous and 4-merous type flowers that are frequently deformed and have streaks or splotches of color in the lower epidermal side of the petals.

The invention relates to a new and distinct plant variety of the milkweed (Asclepiadaceae) family and which has been named the *Hoya carnosa argentea* (cv) Picta by the inventor.

Certain plants of the milkweed family are well known in the foliage plant market. Some of these plants have a compact growth habit in which the nodes on the vines are relatively close together whereas others have a looser growth habit and which the nodes on the vine are further spaced apart. The *Hoya carnosa compacta* variety is exemplary of the milkweed plant family varieties which have a compact growth habit whereas the *Hoya carnosa* variegata and the *Hoya carnosa exotica* varieties exemplify the varieties with a loser growth habit.

Most of the varieties of the milkweed family which are on the market have a smooth, waxy upper epidermal leaf blade part where the color characteristics of the blade are unobscured by waxy formations. In recent years a new and unpatented variety named the *Hoya carnosa* (cv) Verna Jeanette has been introduced to the marketplace and in which the color in the variegated upper epidermal blade part is partially obscured by wax globules that tend to adhere together in splotched and/or streaked areas.

The new variety of plant is related to the *Hoya carnosa* (cv) Verna Jeanette variety but is distinguished from this variety and from its antecedents and related varieties known to the inventor by a growth habit providing specimens which have stems that in color are dominated by red-purple, red and/or yellow-red hues of low value and low chroma prior to becoming glaucous, petioles that in color are dominated by relatively long lasting red-purple, red and/or yellow-red hues, leaf blades which during maturity develop an upper epidermal blade part that in color is partially oscured by waxy splotches and/or streaks and is variegated in a manner providing a green center field area that in color is initially dominated by long lasting red-purple, red and/or yellow-red hues of relatively low chroma and low value and an albino border area that in color is initially dominated by long lasting red-purple, red and/or yellow red hues of higher chroma and value, and a simple umbel inflorscence with mixtures of 5-merous and 4-merous type flowers, that frequently have deformed parts and petals which are streaked or splotched in the lower epidermal side.

The new variety appeared as a sport on a plant specimen of an unnamed variety which was developed from a sport appearing on a plant specimen of the *Hoya carnosa* (cv) Verna Jeanette variety, the sport on the unnamed variety having been under cultivation at a nursery at Winter Garden, Fla. Since the initial discovery of the new variety the new variety has been asexually reproduced by the inventor at the Winter Garden nursery by the propagation of stem cuttings taken from the original plant specimen. Through successive propagations it has been ascertained that plants of the new variety are distinguishable from its antecedents and known related varieties by the characteristics mentioned herein.

The accompanying drawings serve, by color photographic means, to illustrate the new variety and wherein.

Figure 1:
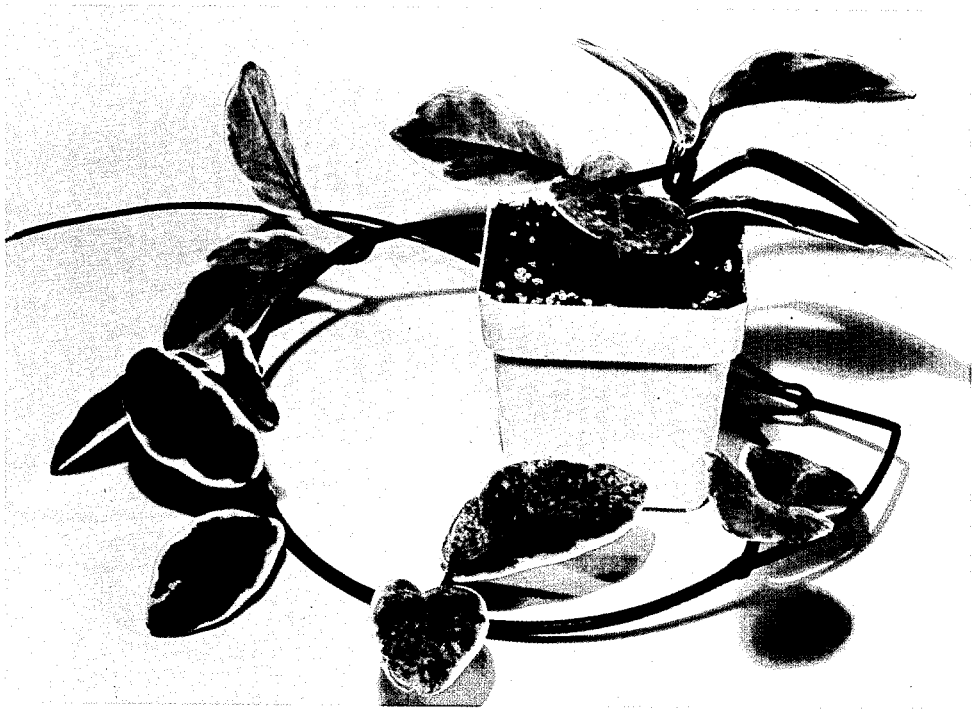
FIG. 1 is a color photograph of a vine cut from a plant specimen of the new variety.
Figure 2:
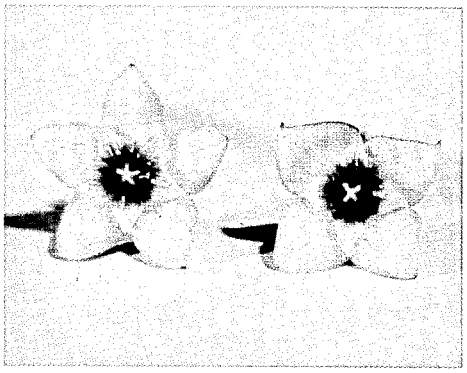
FIG. 2 is a color photograph of two flowers taken from an inflorescence of the new variety.
Figure 3:
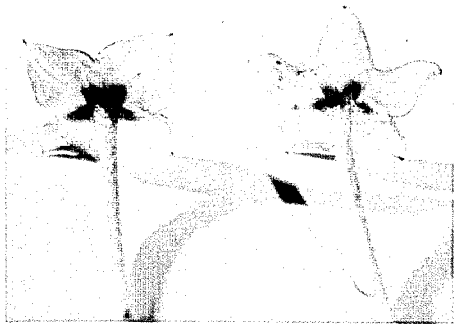
FIG. 3 is a color photograph of the two flower specimens seen in FIG. 2 and showing the streaked and/or splotched color characteristics appearing in the lower epidermal part of the petals.

The following is a detailed description of the new plant variety with colors, unless otherwise clearly indicated by the text, being named in accord with the ISCC–NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Md. On the other hand, when reference is made to hues, values and chromas, reference is being made to the Munsell hues, values and chromas.

*Plant description*

Name: *Hoya carnosa argentea* (cv) Picta.

Origin: A sport on an unnamed plant specimen of a variety developed from a sport that appeared on a plant specimen of the *Hoya carnosa* (cv) Verna Jeanette variety.

Classification:

(*A*) *Botanic.*—(Asclepiadaceae) milkweed family.

(*B*)—*Commercial.*—Foliage plant.

Form: Semisucculent, tropical, twining vine type perennial evergreen with some branching.

Stems:

(*A*) *General.*—Caulescent, fleshy, herbaceous.

(*B*) *Texture.*—Moderately heavy pubescent during immaturity and with age becoming glaucous and ultimately covered thick waxy scale.

(*C*) *Size.*—(1) Diameter: usually between 2 and 6 mm. during first 6 months of growth. (2) Internode: usually between 15 and 80 mm. during first 6 months growth from break with some occurrences of as much as 150 mm.

(*D*) *Color.*—Characterized by color dominated by red-purple, red and/or yellow-red hues of low value and low chroma prior to becoming glaucous. Commonly purplish black (near 10 RP 2/1) blackish purple (near 10 RP 2/1), dark grayish purple (near 10 RP 2/1), dark grayish red (near 2.5 R 2/2) (near 5 R 2/2), blackish red (near 2.5 R 2/2) (near 5 R 2/2), very dark red (near 2.5 R 2/2) (near 5 R 2/2), dark grayish reddish brown (7.5 R 2/2) (10 R 2/2), grayish reddish brown (2.5 YR 3/2) and/or grayish brown (5 YR 3/2) (7.5 YR 3/2).

Leaves:

(*A*) *General.*—Simple, exstipulate.

(*B*) *Arrangement.*—Opposite.

(*C*) *Margins.*—Usually entire.

(*D*) *Venation.*—Pinnate.

(*E*) *Shape.*—(1) General: usually ovate with elliptic tendencies. (2) Leaf apices: usually acute to obtuse. (3) Leaf bases: usually obtuse or rounded.

(*F*) *Petioles.*—(1) General: fleshy. (2) Texture: pubescent and with age becoming glaucous. (3) Size: (a) Diameter—usually between 2 and 5 mm. for mature petioles during first 6 months of growth. (b) Length—usually between 5 and 20 mm. for mature petioles during first 6 months of growth. (4) Color: characterized by color dominated by relatively long lasting red-purple, red and/or yellow-red hues before fading and becoming glaucous. Commonly grayish purplish red (10 RP 4/6) (10 RP 5/6) (5 RP 4/6) (7.5 RP 4/6), dark purplish red (10 RP 3/6) (near 10 RP 2/2) (10 RP 3/4), moderate purplish red (10 RP 5/8), dark grayish purple (near 10 RP 2/2), blackish purple (near 10 RP 2/2), very dark purplish red (near 10 RP 2/2), dark purplish pink (7.5 RP 6/6), dark pink (10 RP 6/6), dark red (2.5 R 3/4), dark grayish red (2.5 R 3/2), dark red (2.5 R 3/4) (5 R 3/4), grayish red (5 R 4/4) (7.5 R 4/4) and/or moderate reddish brown (7.5 R 3/6) (7.5 R 3/4) (10 R 3/4) (10 R 4/4) in immature and newly matured growth. Usually fading to moderate brown (5 YR 4/4) and/or light olive (10 Y 5/4) (10 Y 5/6) prior to becoming glaucous.

(*G*) *Leaf blades.*—(1) General: semisucculent and characterized by variegated leaf blade patterns providing an albino border area surrounding a green center field area in upper and lower epidermal blade parts. (2) Texture: (a) Upper epidermis—slightly pubescent during immaturity and sparcely pubescent during maturity with splotches and/or streaks of color obscuring waxy formations which appear as the blade is maturing. (b) Lower epidermis—moderately pubescent and heavily glaucous at maturity. (3) Size: (a) Length—usually between 30 and 125 mm. in mature leaves about 6 months old. (b) Maximum width—usually between 15 and 70 mm. in growth about 6 months old. (4) Color: (a) Upper and lower epidermal albino border areas—characterized by color initially dominated by relatively long lasting red-purple, red and/or yellow-red hues of higher chroma and value than in green center field of upper epidermal area and which gradually fade from area. Commonly moderate purplish red (10 RP 4/10), moderate pink (10 RP 6/8), moderate red (2.5 R 5/8), light pink (near 2.5 R 8/4) (near 5 R 8/4), moderate pink (near 2.5 R 8/4) (near 5 R 8/4) (10 RP 7/6) (5 R 7/6) (2.5 R 7/6), deep pink (2.5 R 6/8), strong yellowish pink (7.5 R 7/8), light yellowish pink (near 10 R 8/4) (near 2.5 YR 8/4), moderate yellowish pink (near 10 R 8/4) (near 2.5 YR 8/4) (near 5 YR 7/6), moderate orange (near 5 YR 7/6), pale orange yellow (near 7.5 YR 8/6) (near 10 YR 8/6) (10 YR 8/4) (7.5 YR 8/4), light orange yellow (near 7.5 YR 8/6) and/or moderate orange yellow (near 7.5 YR 8/6) (near 10 YR 8/6) in immature and young mature growth. Commonly pale yellow (2.5 Y 9/4) (near 2.5 Y 9/2) (near 5 Y 9/2) (near 7.5 Y 9/2) (5 Y 9/4), light yellow (5 Y 9/6) (near 5 Y 9/8), brilliant yellow (near 5 Y 9/8), yellowish white (near 5 Y 9/2) (near 2.5 Y 9/2) (near 7.5 Y 9/2), light greenish yellow (7.5 Y 9/6), pale greenish yellow (7.5 Y 9/4) and/or pale yellow green (10 Y 9/2) in older and mature growth. (b) Upper epidermal green center field area—characterized by color initially dominated by long lasting red-purple, red and yellow-red hues of low value and low chroma in immature and young mature growth. Commonly purplish black (near 10 RP 2/1), blackish purple (near 10 RP 2/1), dark grayish purple (near 10 RP 2/1), reddish black (near 2.5 R 2/1), blackish red (near 2.5 R 2/1) (near 5 R 2/2), dark grayish red (near 2.5 R 2/1) (near 5 R 2/2), very dark red (near 5 R 2/2), dark grayish reddish brown (10 R 2/1) (7.5 R 2/2), grayish reddish brown (2.5 YR 3/2), brownish gray (10 YR 3/1), grayish brown (5 YR 3/2) (7.5 YR 3/2) and/or dark grayish yellowish brown (10 YR 3/2) in immature and newly mature growth. Commonly moderate olive green (7.5 GY 4/4) (7.5 GY 4/6) (5 GY 4/4), moderate yellow green (7.5 GY 7/4) (2.5 GY 5/6) (5 GY 5/6), grayish olive green (7.5 GY 4/2) and/or grayish yellow green (7.5 GY 7/2) in fully matured and older growth. (c) Lower epidermal green center field area—usually moderate yellow green (5 GY 6/4) (2.5 GY 5/4).

Inflorescence:

(*A*) *Form.*—Simple umbel inflorescence with mixture of 5-merous and 4-merous type flower and occasionally 3-merous type flowers, the flowers frequently having deformed parts and also having minute bracts.

(*B*) *Peduncles.*—(1) General: hard, fleshy. (2) Texture slightly pubescent and with age becoming glaucous and ultimately covered with thick waxy scale. (3) Size: (a) Length—usually between 10 and 60 mm. at maturity. (b) Diameter—usually between 1 and 5 mm. at maturity. (c) Color—commonly grayish reddish brown (2.5 YR 3/2), grayish brown (5 YR 3/2) and/or brownish gray (5 YR 3/1).

(*C*) *Pedicels.*—(1) General: Soft, fleshy. (2) Texture: sparcely pubescent. (3) Size: (a) Length—usually between 30 and 45 mm. at maturity. (b) Diameter—usually between .7 and 3.5 mm. at maturity and tending to taper to smaller dimension at proximal end. (4) Color: commonly dark purplish pink (5 RP 6/8), moderate red (5 R 5/10), moderate purplish red (5 RP 5/8) (5 RP 4/8) (7.5 RP 4/8) at maturity.

(*D*) *Flowers.*—(1) General: perfect, actinomorphic mixture of predominately 5-merous type flowers with 4-merous and occasionally 3-merous type flowers with hypogynous perianth and alternate sepal-petal and petal-corona segment arrangements. (2) Size: usually between 14 and 18 mm. in overall diameter. (3) Calyx: (a) General—separate, valvate sepals. (b) Sepal texture—(1) Upper epidermis: smooth and glabrous. (2) Lower epidermis: sparcely pubescent. (c) Sepal color—grayish purplish red (7.5 RP 4/6) (7.5 RP 5/6) (10 RP 4/4) (7.5 RP 4/4). (4) Corolla: (a) General—valvate and rotate with interpetal basal fusion for about ½ petal length. (b) Petal texture—(1) Upper epidermis: very dense velvety pubescence. (2) Lower epidermis: glaucous and waxy. (c) Petal color—(1) Upper epidermal side: commonly grayish purplish pink (2.5 RP 7/4) (5 RP 7/4) (7.5 RP 7/4), pale pink (5 R 9/2) and/or pale purplish pink (5 RP 8/4). (2) Lower epidermal side: streaks and/or splotches of moderate purplish red (5 RP 5/8) (5 RP 5/10), moderate purplish pink (5 RP 7/6) and/or dark purplish pink (7.5 RP 6/6). (5) Corona: (a) General horn-like segments which are adnate to stigma and corolla and crested at their proximal ends. (b) Segment texture—hard, smooth, waxy and glabrous. (c) Segment color—(1) Proximal end: commonly grayish purplish red (5 RP 4/6), dark grayish purple (5 RP 3/2), dark purplish red (5 RP 3/4) and/or moderate purplish red (5 RP 4/8) and merging with distal end color. (2) Distal end: commonly yellowish white (10 YR 9/1) (near 10 YR 9/2) and/or pale orange yellow (near 10 YR 9/2) and merging with proximal end color. (6) Androecium: (a) General—5-merous pollinium pairs partially enclosed by expanded translucent parenchymatous translators and attached to stigma through corpuscula located between adjacent segments and with pollinia and translators rising above corpuscula and stigma in conberging conical arrangement in 5-merous type flowers with 4-merous and 3-merous pollinium pairs in 4-merous and 3-merous type flowers. (b) Pollinium color—brilliant yellow (near 5 Y 8/10), strong yellow (near 5 Y 8/10) and/or vivid yellow (5 Y 8/12). (7) Gynoecium: (a) General—compound and apocarpous pistil with common stigma. (b) Stigma—5-lobed and waxy for 5-merous type flower and similar arrangements for 4-merous and 3-merous type flowers. (c) Style—lacking. (d) Ovary—two monocarpellate ovularies with auxillary placentation of ovules in 5-merous type flowers.

The above description is based on observations of well fertilized plants of less than two years old from initial propagation and which were grown under 85% shaded nursery conditions in the Winter Garden, Fla. area and wherein temperatures range approximately from 60–85° F. during the winter months and from 75–95° F. during the summer months.

The following is a general description of a plant specimen of the new variety which was propagated from a stem cutting, the description being taken in the month of January, about six months after the cutting was first planted in a nursery at Winter Garden, Fla.

Stem:

(*A*) *Length.*—About 495 mm. from break to tip.

(*B*) *Number of nodes.*—7 mature nodes plus 3 with embryonic leaves.

(*C*) *Diameter.*—Ranges from about 1½ mm. at tip to about 4 mm. near the rooted cutting.

(*D*) *Internode distance.*—Varies from about 32 mm. to about 80 mm.

(*E*) *Color.*—Very dark red (near 2.5 R 2/2), dark grayish red (5 R 3/2), dark grayish reddish brown (10 R 2/2) and grayish reddish brown (2.5 YR 3/2).

Leaves:

(*A*) *Number of nonembryonic leaves.*—12 mature plus two newly immature (less than 15 days old).

(*B*) *Petioles.*—(1) Diameter—vary from 2 to 3 mm. at maturity. (2) Length—vary from 8 to 13 mm. at maturity. (3) Color—moderate reddish brown (7.5 R 3/6) (10 R 4/4), dark grayish red (2.5 R 3/2), grayish purplish red (10 RP 5/6) in growth less than 4 months old and light olive (10 Y 5/6) (10 Y 5/4) in older growth.

(*C*) *Blades.*—(1) Maximum width—vary from 22 to 43 mm. at maturity. (2) Maximum length—vary from 32 to 62 mm. at maturity. (3) Color—(a) Upper and lower epidermal border areas—moderate pink (10 RP 7/6), moderate red (2.5 R 5/8), deep pink (2.5 R 6/8) and strong yellowish pink (7.5 R 7/8) in growth less than 2 months old with older growth being light yellow (5 Y 9/6), pale yellow (5 Y 9/4) (2.5 Y 9/4), light greenish yellow (7.5 Y 9/6) and yellowish white (near 7.5 Y 9/2). (b) Upper epidermal green center field—very dark red (5 R 2/2), dark grayish reddish brown (7.5 R 2/2), grayish brown (5 YR 3/2) (7.5 YR 3/2) in growth less than 2 months old and moderate olive green (7.5 GY 4/6), moderate yellow green (7.5 GY 7/4) and grayish yellow green (7.5 GY 7/2) in older growth. (c) Lower epidermal green center field—moderate yellow green (5 GY 6/4) (2.5 GY 5/4) in mature growth.

The following is a general description of an inflorescence which appeared on a vine about 2 years old.

Number of flowers: 17 with 7 undeformed 5-merous type flowers, 6 variously deformed 5-merous type flowers and 4 4-merous type flowers.

Peduncle:

(*A*) *Size.*—(1) Length: about 32 mm. (2) Diameter: about 3 mm.

(*B*) *Color.*—Grayish reddish brown (2.5 YR 3/2), grayish brown (5 YR 3/2).

Pedicels:

(*A*) *Size.*—(1) Length: vary from 35 to 40 mm. (2) Diameter: tapering from about 3 mm. at distal end to about 1 mm. at proximal end.

(*B*) Color.—Dark purplish pink (5 RP 6/8), moderate red (5 R 5/10), moderate purplish red (7.5 RP 4/8).

Flowers:

(*A*) *Size.*—Vary from 16 to 17 mm. in diameter for both 4-merous and 5-merous type flowers.

(*B*) *Sepal color.*—Grayish purplish red (7.5 RP 4/6) (7.5 RP 5/6) (7.5 RP 4/4) in both upper and lower epidermis.

(*C*) *Petal color.*—(1) Upper epidermal side: pale pink (5 R 9/2), grayish purplish pink (5 RP 7/4) (2.5 RP 7/4) and pale purplish pink (5 RP 8/4). (2) Lower epidermal side: streaks and/or splotches of moderate purplish pink (5 RP 5/8) (5 RP 7/6), dark purplish pink (7.5 RP 6/6).

(*D*) *Corona segment color.*—(1) Proximal end: dark grayish purple (5 RP 3/2), grayish purple (5 RP 4/6), dark purplish red (5 RP 3/4) and moderate purplish red (5 RP 4/8) and merging with distal end color. (2) Distal end: yellowish white (10 YR 9/1) (near 10 YR 9/2) and pale orange yellow (near 10 YR 9/2) and merging with proximal end color.

I claim:

1. The new and distinct plant variety of the milkweed family substantially as herein described and characterized in particular by a loose growth habit providing specimens which have stems that in color are dominated by red-purple, red and/or yellow-red hues of low chroma and low value prior to becoming glaucous, which have petioles that in color are dominated by relatively long lasting red-purple, red and/or yellow-red hues, which have an inflorescence with mixtures of 5-merous and 4-merous type flowers that frequently have deformed parts and petals which are streaked and/or splotched with color in the lower epidermal side, and which have leaf blades with color in the upper epidermal part partially obscured by waxy splotches and/or streaks and with variegated patterns providing a green center field and surrounding albino border areas, the color of the green center field being dominated by relatively long lasting red-purple, red and/or yellow-red hues of relatively low chroma and low value and the color of the albino area being dominated by relatively long lasting red, red-purple and/or yellow-red hues of generally higher chroma and value than the green center field area.

No references cited.

ROBERT E. BAGWILL, Primary Examiner